(12) United States Patent
Ruepp

(10) Patent No.: US 6,344,217 B1
(45) Date of Patent: Feb. 5, 2002

(54) PUTAMEN OVI

(75) Inventor: Michel O. Ruepp, Remscheid (DE)

(73) Assignee: AAR Pharma Adler Apotheke (DE)

(*) Notice: Subject to any disclaimer, the term of this patent is extended or adjusted under 35 U.S.C. 154(b) by 0 days.

(21) Appl. No.: 09/065,492

(22) Filed: Apr. 24, 1998

Related U.S. Application Data (63) Continuation-in-part of application No. 08/765,623, filed as application No. PCT/EP95/02531 on Jun. 28, 1995, now abandoned.

(30) Foreign Application Priority Data

Jun. 28, 1994 (DE) .............................. 4422613
Nov. 21, 1997 (DE) .............................. 19751681

(51) Int. Cl.⁷ .............................. A61K 35/54
(52) U.S. Cl. .............................. 424/581
(58) Field of Search .............................. 424/543, 561, 424/581, 687

(56) References Cited

U.S. PATENT DOCUMENTS 3,558,771 A 1/1971 Balassa

FOREIGN PATENT DOCUMENTS

| CH | 193065 | 1/1938 |
|----|--------|--------|
| EP | 0347899 | 6/1989 |
| FR | 849055 | 12/1961 |
| GB | 2218906 | 11/1989 |
| RU | 1754104 | 1/1989 |

OTHER PUBLICATIONS

Römpp Chemielexikon (1993), p. 4301 "Sterilisation" [sterilization] —English Translation.
Römpp Chemielexikon (1997), p. 322 "Autoklaven" [autoclaves] —English Translation.
Chemical Abstracts, vol. 117 (1992) pp. 456, Abstr. 33411. Properties of eggshell as a raw material for cosmetics,: Ishizuka, et al.
Onoda, JP 59/137415, Calcium prep. for oral medicinal use—comprising finely crushed dried egg shells (Patent abstract only).
Li CN 1079149, "Preparation of a calcium comp. from egg shells—for use as an additive in food or medicine" (patent abstract only).
Cano and Colome, Microbiology, 1986, West Publishing Co., New York, pp. 1158–59 & 1161.

*Primary Examiner*—Jean C. Witz
(74) *Attorney, Agent, or Firm*—Brobeck, Phleger & Harrison, LLP (57) ABSTRACT

The present invention pertains to a method for the preparation of putamen ovi, putamen ovi having a defined grain size distribution, and to the use of putamen ovi for the treatment of calcium deficiency and other disease conditions.

15 Claims, 1 Drawing Sheet

FIG. 1

PUTAMEN OVI

This application is a continuation in part of application Ser. No. 08/765,623, filed Dec. 27, 1996, now abandoned, which is the U.S. National Phase of application PCT/EP95/02531, filed Jun. 28, 1995, designating the U.S., the text of which is incorporated herein in its entirety.

BACKGROUND OF THE INVENTION

1. Field of the Invention

The present invention pertains to a method for the preparation of putamen ovi, to putamen ovi having a defined grain size distribution, and to the use of putamen ovi for the treatment of various diseases. Additionally, the present invention pertains to the use of processed putamen ovi for the preparation of orally applicable medicaments and locally applicable bone replacement.

2. Review of Related Art

Egg shell as a medicament has been used since 1930. Formulations made of egg shells are still being used as a mineral and trace element supplying agent for the substitution of, in particular, calcium.

According to Römpp Chemielexikon, 9th edition, 1990, page 1079, item "Eier" ("eggs"), the egg-shell of chicken eggs has a thickness of from 0.2 to 0.4 mm and is white or brown in color, depending on the breed. It is composed of a protein framework (protein-mucopolysaccharide complex) in which calcium carbonate as well as a minor amount of Ca and Mg salts are incorporated. The shell contains pores (7000–17,000 per egg) which are filled with protein fibers. The eggs of other bird species, such as goose, duck, pigeon or quail, are much less important than chicken eggs and are always indicated according to their origins. The shell has a dry mass content in the order of 98.4% which consists of 3.3% of proteins and 95.1% of minerals.

From SU 1 754 104, the use of egg-shells as a dentifrice is known. The use of this preparation is that of a dentifrice. It contains an allegedly caries-inhibiting film with reduced abrasive properties. This dentifrice contains only a very small and non-activity-determining proportion of egg-shells as an adjuvant. The egg-shell powder is not present as a monosubstance, but is embedded in sodium hydrogencarbonate (35–45% (m/m)) and is not taken up by the organism.

In CH 193 065 A, a liquid tonic is described which is rich in egg yolk, and thus particularly rich in cholesterol, and has high sugar and alcohol contents, but contains little egg-shell components. This is due to the preparation method. The finished emulsion contains from 2 to 3% of egg-shell components in the form of citrates—but only those which are dissolved or emulsified. This preparation contains only particular fractions of egg-shell. Due to its high proportion of cholesterol, sugar and alcohol, this tonic is not acceptable therapeutically in view of its clear potential of load on physiological feedback control systems.

According to FR-A-0 649 055, the egg-shells are sterilized with 20% ethylene oxide at 50 ° C. under a pressure of 5 atmospheres. This method enables a germ reduction rather than a complete sterilization which would be necessary to provide a product in conformity with the requirements of a human health product due to the presence of pathogenic bacteria, spores, etc. in the natural product egg shell.

The preparation described in GB 2 218 906 is employed for the treatment of dermal lesions. Finely ground egg-shells are processed into a preferably liquid formulation to be used orally or topically which in particular also includes essences, paraffin and various waxes and paraffin oils. The use of this preparation with eczema and allergic skin conditions is not acceptable for oral and topical application since egg-shells, due to their protein base, have a high allergenic potential themselves and may trigger typical skin irritations and increase existing syndromes of certain dermal lesions of allergic nature. Heating the egg-shells for sterilization by means of microwaves over a period of 6 minutes is inadequate for eliminating pathogens.

In EP 0 347 809 A2, a sterilization method for egg-shells is described. The sterilization method reported is unsuitable for eliminating the possible presence of pathogenic bacteria, spores, fungi and protozoans. The sterilization of egg-shell powder with dry air at 120° C. for about 1 hour is not suitable for effecting a safe reduction of pathogenic germs and to counteract a loss in active ingredients. An increase in temperature, especially in the range of $\geq 150°$ C., for more than 1 hour destroys the biological carriers with membrane transit ability for an effective transport of minerals in compact and spongy substances. Following this thermal exposure, the egg-shell powder exhibits the biological effects of calcium carbonate with respect to the $^{45}$Ca incorporation rate.

Various formulations comprising egg-shell powder have been examined in U.S. Pat. No. 3,558,711, especially in rats with topical application on open wounds. An improved wound healing has been achieved as compared to the control animals. In this document, no suitable sterilization method is reported which would not affect the therapeutic effectiveness of the egg-shells. An oral application of egg-shell powder is not suggested in this patent.

In Chemical Abstracts, vol. 117, 1992, Ref. 33411x, egg-shell powder is processed into cosmetic preparations under the action of lactic acid. The calcium lactate products thus generated are embedded in a protein film. This lactate emulsion is processed into a cosmetic cream. In much the same way as preparation 1 (SU 1754 104), it only contains particular fractions of egg-shell which are topically applied.

In addition, there has been many decades of experience in the preparation of specialties, in particular in the sterilization without activity losses, namely: if a temperature of 80° C. is exceeded in the sterilization of the egg-shell, then the biological carrier with membrane passage ability for the minerals is destroyed, so that the activity of the thermally destroyed product corresponds to that of calcium carbonate with respect to the $^{45}$Ca incorporation rate. On the other hand, this temperature alone is not sufficient to completely free the porous, heat-insulating raw material egg-shell/egg-shell powder from pathogenic bacteria, spores, fungi and protozoans the presence of which is to be expected due to fecal contamination, especially when in addition the storage conditions are unfavorable.

The prior art shows that the egg shell is formulated in the form of standardized, orally applicable preparations and is used for calcium substitution. However, there is still an need for an especially processed orally applicable medicament and locally applicable bone replacement.

SUMMARY OF THE INVENTION

According to the invention, it has been found that the use of putamen ovi surprisingly has advantages over the use of pure calcium carbonate in various conditions of disease. However, a particular problem in the use of putamen ovi as a medicament is to provide a standardized sterile medicament having a defined grain size.

In a first embodiment of the present invention, the above problem is solved by a method for the preparation of putamen ovi having a grain size of less than 0.1 mm wherein
a) egg-shells, especially from *Gallus domesticus,* are washed with water or an aqueous solution containing disinfectants and/or tensides with stirring at room temperature or elevated temperature;
b) the egg-shells having been cleaned from contaminants are subjected to a germ count reduction process or sterilization process;
c) the egg-shells are dried; and
d) the egg-shells are crushed to the desired grain size following or during the drying.

In another embodiment of this invention, an especially processed orally applicable medicament and locally applicable bone replacement is provided by the use of the central palisade zone of egg shells which is freed from the shell membrane, or from the shell membrane and the shell matrix, by proteases or alkaline denaturation, followed by purification, or by the use of the palisade matrix which is obtained either by decalcification or by means of aqueous and/or organic solvents, as well as by means of critical gases ($CO_2$).

In yet another embodiment of this invention, methods are provided for the use of processed putamen ovi (egg shell of *G. domesticus*), in particular saccharide-containing granules of micronized egg shells (PO), egg shell components of the central palisade zone (POM), shell matrix with organically bound minerals (MPM), for the preparation of orally applicable medicaments for the treatment and prevention (protection) of organ and tissue damages caused by radiation (radioprevention, radioprotection), infections (infection prophylaxis) and chemically (chemoprevention, chemoprotection), especially of the O-MALT (mucosa associated lymphoid tissue) system of the small intestine (inflammatory diseases, Enteritis regionalis Crohn), the bone marrow (bone marrow aplasia), of bone and cartilage genesis disorders, of diseases of the locomotor system, of disease of the thymus (dysfunction, aplasia or hypoplasia), the spleen (dysfunction) and the lymph nodes (aplasia or hypoplasia due to medicament or radiation caused damages), the liver (atrophy, necrosis), the pancreas (insufficiency of the exocrine, secretory function of proteases, esterases, carbohydrases and nucleases, as well as insufficiency of the endocrine function of the islets of Langerhans and the carbohydrate metabolism) and the kidneys (insufficiency), and in general immunosuppressed conditions, for cellular immunostimulation, for the therapy of leucocytopenia, granulocytopenia, lymphocytopenia, thrombocytopenia, erythrocytopenia and in immunoglobulin deficiency conditions, also due to AIDS and tumors, as well as for the therapy of hyperlipoprotein-emias and hyperlipidemia; further, for the treatment of primary or secondary disorders or damages of chondral or desmal ossification, also in combination with sodium fluoride and hormones, especially estrogens (new generation estrogens, e.g., estrogen sulfamate), calcitonin, pyrophosphates (biphosphonates) and vitamins, especially vitamin D ($D_3$ and dihydroxycholecalciferol), of the bony substance with external Substantia corticalis (lamellar bones) and internal Substantia spongiosa (framework of minute trabeculae) as well as bone marrow due to a reduction of all hematopoietic cell forms (bone marrow aplasia, depression or bone marrow metastases) due to a cytostatic or radiologic therapy or after radiation accidents, of the skeleton including osteocytes, intercellular substance with collagenous fibrils and calcified cement, of bone metabolism including the function of osteoclasts and osteoblasts, the balance between bone absorption and formation (bone tissue remodeling); for local and oral application for the reconstruction of bone deficiencies, in fracture healing, in the filling of bone damages after tumor operations, and for the removal of bone damages in oral surgery and plastic surgery of the face; further, for the treatment of bone necrosis due to irradiation and prolonged corticoid medication.

BRIEF DESCRIPTION OF THE DRAWINGS

For a more complete understanding of the present invention, and some of the advantages thereof, reference is now made to the following descriptions taken in connection with the accompanying drawings in which.

DETAILED DESCRIPTION OF THE INVENTION

Putamen ovi within the meaning of the present invention comprises hygienically processed egg-shell, in particular from *Gallus domesticus*.

Bone structure is subject to a variety of regulation mechanisms. It is generally known that the essential minerals calcium, phosphorus and magnesium participate in the bone metabolism. In addition, a number of particular trace elements, such as manganese, copper and zinc, are also required as cofactors of collagen and mucopolysaccharide synthesis for the maintenance of metabolic equilibrium. Deficiency in such essential trace elements leads to a pathophysiological condition with interference of enzymatic reactions in the cells of the hard tissue. These adverse effects on the bone metabolism can also consecutively spread to the immune system.

If human and animal hard tissues are compared under these aspects, a strikingly similar spectrum of minerals and trace elements can be detected in bones, teeth, and also in putamen ovi (e.g., egg shell, *G. domesticus*) which is formed outside the bones by membrane passage. In a comparison between bones and putamen ovi (PO), this correspondence does not only concern the inorganic, but also certain organic compounds, such as mucopolysaccharides based on chondroitin sulfate and hyaluronic acid.

In the case of Gallus species, minerals and trace elements from the PO matrix membrane are presented to the skeleton system of the developing organism in a bioavailable manner during the embryonic phase, which process can be compared to the osteoneogenesis of the mammal organism including humans.

The present invention provides the beneficial matter from egg shells in a particularly useful form. In particular, the active components of egg shells are provided for use in the following forms:

1. egg shell components of the central palisade zone, freed from inner and outer shell membranes (PO)
2. egg shell components of the central palisade zone, freed from inner and outer shell membranes and from the shell matrix of the palisade zone (POM)
3. shell matrix of the palisade zone with organically bound minerals (MPM).

Production of Putamen Ovi

The process for the preparation of putamen ovi (an organotherapeutical agent, from a medical point of view), having a grain size of less than 0.1 mm, may be realized by using the egg shells, preferably from fresh eggs (not from eggs subjected to long-term storage), stored under controlled conditions.

During egg shell selection, each egg is examined for quality (e.g., for its integrity and degree of freshness) which may be performed by individual transillumination of each egg, or any other known technique.

The eggs are broken, either by hand or by a mechanical means, and the egg shells are collected and may be subjected to deep freezing (i.e., about −25° C.). Egg-white and egg-yolk from these eggs may be recovered for routine use. Preferably, the shells used in this invention come from fresh eggs, so the white and yolk are suitable for use by bakeries and confectioneries. It is recommended that further processing of the egg shells should be completed no more than four (4) days from breaking, preferably after an extensive analytical examination of the egg shell by a visual and olfactory test (fresh egg odor should be retained).

Figure 1:
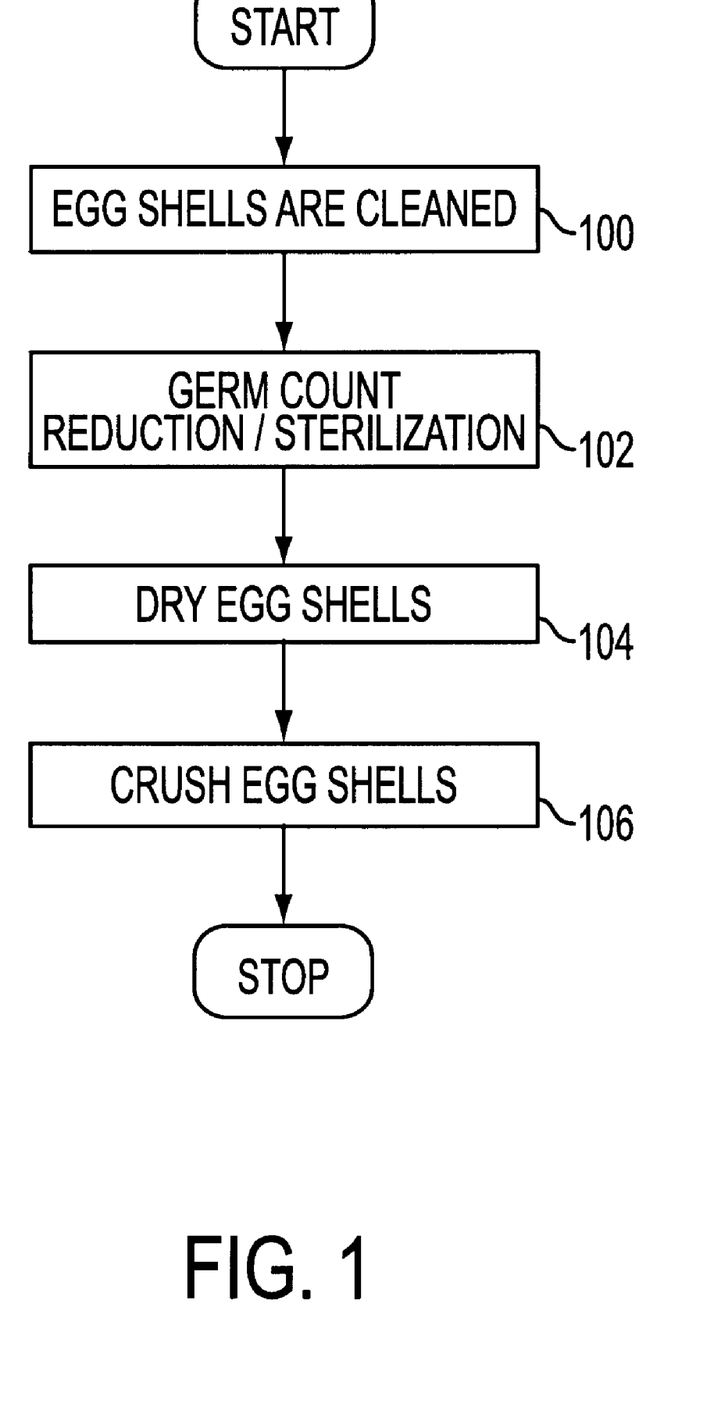
FIG. 1 depicts a flowchart of the processing of putamen ovi according to the present invention.

Referring to FIG. 1, a flowchart depicting the method for the preparation of putamen ovi according to the present invention is provided. In step 100, egg shells are cleaned at or above room temperature. These egg shells may be from *G. domesticus;* however, other egg shells may also be used. The cleaning may be effected by washing the shells with purified water (aqua purificata). For example, egg shell batch sizes of 50 to 100 kg usually require about 250 l of water for cleaning. This may be done once, or it may be repeated several times, and the egg shells may be stirred during the cleaning. Cleaning agents, such as surfactants, may be used. Once the cleaning step is completed, the suspended matter that results from the cleaning is drawn off.

In step 102, the cleaned egg shells are subjected to a germ count reduction process or sterilization process. A number of germ count reduction processes or sterilization processes are suitable, such as hot air drying, tyndallization, treatment with ionizing or non-ionizing radiation, and gas sterilization. In a preferred embodiment of the present invention, the germ count reduction process or sterilization process is accomplished by an autoclave treatment, as described below.

Depending on the autoclave time, two different products can be obtained. By autoclaving for three hours or less, egg shell components of the central palisade zone can be obtained which are free from the inner and outer shell membrane. This composition may be referred to herein as "PO".

When the autoclave treatment is preformed for 6 to 10 hours, egg shell compositions of the central palisade zone will be obtained which are not only freed from the inner and outer shell membrane, but further are freed from the shell matrix of the palisade zone. The composition resulting from such treatment is referred to herein as "POM". PO as well as POM show an osteoneogenic effect when administered orally, and this effect has never before been described. Furthermore, POM is suitable as the base of a formulation for local application as a bone substitute.

The autoclave treatment is preferably performed discontinuously; that is, air and water vapor are completely removed at given intervals and replaced with freshly prepared steam. The function of the autoclave treatment is not only to inactivate microorganisms and eliminate contaminants and storage protecting agents, but also to inactivate a toxic and allergic potential which is associated with the presence of defined, and partly denatured, ovoproteins. By the use and the relatively long time of action of the live steam, membrane and palisade proteins and glucoproteins are dissolved as a gel and essentially eliminated, particularly by the discontinuous operation of the process.

The egg shells are subsequently dried and crushed to the desired grain size following or during the drying. In step 104, the egg-shells are dried at elevated temperature. This especially involves the evaporation of the water contained in the pores. Particularly preferred drying methods include vacuum drying or freeze-drying as well as drying at increased temperatures.

In an alternative embodiment, sterilization step 102 and drying step 104 may be accomplished simultaneously. This embodiment of the present invention uses hot air drying at a temperature above the boiling point of water, especially at a temperature of at least 150° C., for at least 3 hours in which sterilization and drying are conjoined in one process step.

Subsequent to drying step 104 or during the drying, the egg-shells are crushed in step 106 to the desired grain size of less than 0.1 mm. It is particularly preferred according to the present invention to crush the dried egg-shells with a grinding disk followed by screening with a mesh size of 0.1 mm×0.09 mm. To obtain different grain sizes, different grinding aggregates and/or different mesh sizes may be used.

In a further embodiment of the present invention, other screening methods, such as air classification, may also be used.

By means of the present invention, it is possible to prepare putamen ovi having a defined grain size in which a major portion of the biologically active materials contained in the egg-shell in addition to calcium carbonate are conserved. A further embodiment of the present invention is putamen ovi obtainable by a method as defined above and having a grain size distribution of 35% by weight of >0.05 mm and 65% by weight of <0.01 mm.

The POM egg shell components can be prepared not only by the process above (POMI), but also by enzymatic treatment ($POM_2$) or by alkaline treatment ($POM_3$). With enzymatic treatment, the starting material is PO, which may be incubated with a solution of proteases (e.g., 1 to 10% proteolytic enzymes), buffered at suitable pH (e.g., 7 to 8) and temperature (e.g., 30 to 40° C.) for a period of 24 to 72 hours, and then again subjected to autoclave treatment for 1 to 3 hours for purification.

With alkaline treatment, the starting material is PO, which is mixed with boiling alkali (e.g., aqueous 1–5% NaOH solution), followed by purification by means of autoclave treatment for 1 to 3 hours.

The shell matrix of the palisade zone, MPM, with organically bound mineral substances can be isolated by at least three methods: (1) the mineral-containing glycoproteins ($MGP_1$) are dissolved as gels by autoclave treatment, and $MGP_1$ is isolated from the exchanged aqueous phase by thermal, vacuum, and/or freeze drying; (2) the mineral-containing glycoproteins ($MGP_2$) are dissolved as gels by means of aqueous and/or organic solvents or with supercritical fluids ($CO_2$ extraction) and then isolated by thermal, vacuum, and/or freeze drying; or (3) $MGP_3$ (denatured) is obtained in the preparation of $POM_3$. After alkaline treatment of POM with boiling 1–5% NaOH solution, the solution is filtered off from the residual shell skeleton and neutralized. Then, the $MGP_3$ is isolated by vacuum and/or freeze drying.

Therapeutic Formulation of Putamen Ovi

The putamen ovi thus provided can be processed, using suitable known adjuvants and vehicles, into a medicament which may be employed for various pathologic calcium deficiency conditions.

In particular, it has been found that a natural substance therapeutic agent obtained as described herein contains minor amounts of other essential minerals in addition to calcium, such as iron, fluorine, potassium, silicic acid, magnesium. In addition, it contains biologically generated active compounds, such as enzymes, porphyrin, sterols, vitamin $D_3$, along with the biologically important trace elements copper, molybdenum, selenium and zinc; some of the enzymes, porphyrins, and sterols survive autoclaving.

Putamen ovi according to this invention provides calcium in a biologically bound form and thus serves a carrier function for a very effective resorption from the intestine into the blood. Good resorption of the minerals, the organic active compounds, and the trace elements by the organism is a precondition for the clear effectiveness of putamen ovi in bone diseases and concomitant anemia.

In the PO test preparation, the biologically active organic and the mainly complex-bound inorganic components, such as calcium, iron, fluorine, potassium, silicic acid, magnesium, copper, molybdenum, selenium, zinc etc., which are necessary for bone metabolism, are contained in a mostly bioavailable state for possible therapeutic applications.

Preparation of PO according to this invention will typically comply with validated requirements for the active component with respect to selection (quality, purity), processing (purity, sterility) and galenics (standardization, bioavailability) are observed.

PO, POM and MPM may be formulated as powders, granules or pastes for the oral and local application as bone cement or in bone remodeling and implantation, as well as for bone replacement with an osteoneogenesis-active potential for the well-aimed local bone formation. The active ingredient according to this invention may be formulated in a medicament in the form of putamen ovi pulvis and in extracted form, by aqueous and/or organic and/or supercritical solvents, especially carbon dioxide, as powder, granules, capsule, tablet, coated tablet, pastille (lozenge) or paste.

Therapeutic Use of Patamen Ovi

In PO therapy, the focus is on:
1. the prevention of certain spontaneous fractures in typical positions in static insufficiency of the skeleton by an improvement of the microarchitecture due to induction and stimulation of local microcallus formation;
2. the stimulation of osteoneogenesis and hematopoiesis;
3. a chemoprevention in an accompanying therapy with chemically defined diuretics, cytostatic agents and corticoids (inhibition of substance-specific osteoporosis/bone marrow aplasia effects), and improvement of the tolerance for an accompanying hormone treatment;
4. reduction of the loading pains of the cerebral column and the joints, which often set in early.

The biologically important trace elements promote the development of a sound bone system and beneficially affect disturbed bone metabolisms. With bone fractures, a significant shortening of the healing is achieved which is caused by a quicker callus and bone formation.

Osteopenia (loss in bone tissue) is not a disease but the age-dependent destruction of bone tissue which begins about from the 30th year of life and may amount up to 1.5% per year. Thus, up to the 70th year of life, a loss of about ⅓ of the bone mass occurs without danger to the bone skeleton. However, if calcium supply is insufficient, such as in calcium resorption disorders or metabolic disorders, the organism withdraws calcium from the bones. Such withdrawal leads to a reduction in the bone substance, although not all bony organs are equally endangered. The spongy bones of the vertebral bodies (spinal column) are attacked first, the tubular bones of arms and legs only later. Therefore, the spinal column is particularly in danger, with the risk of spine deformation. The muscles try to counteract such changes in the spinal column, and the additional muscular action sooner or later results in muscular pain. Therefore, muscular pain is present in osteoporosis.

In one pilot study, it could be proven that the addition of PO to the medium in a culture of human osteoblasts could induce the latter to increased formation of type I collagen as well as osteopontin. In a pilot study in rabbits, the local application of extracorporal shock waves to the perineal bone induces a restricted neogenesis of bone tissue in the spongy substance. When PO is additionally orally administered, the extent of this neogenesis is increased, and the additional course of remodeling is accelerated.

Therefore, the putamen ovi obtained according to the invention is especially useful in the treatment of bone marrow development disorders, bone marrow dysfunctions, dyshematopoiesis, osteopenia, osteoporosis, dental build-up disorders, spasmophilia, bone fractions, callus formation and calcium deficiency symptoms during growth, pregnancy, postmenopause and nursing period. This bone remodeling and implantation is a complex process of bone regeneration and remineralization which is inseparably connected with a local improvement of blood supply (stimulation of hemato-, angio- and osteogenesis) by putamen ovi alone and/or in combinations such as the combinations mentioned in Example 2. Putamen ovi according to this invention may be administered concurrently with sodium fluoride and hormones, especially estrogens, calcitonin, pyrophosphates (biphosphonates) and vitamins, especially vitamin D ($D_3$ and dihydroxycholecalciferol).

Benefits of therapy with putamen ovi according to the present invention include:

1. the general increase in defined immunocompetent cells in the bone marrow, in primary and secondary lymphatic organs and in the terminal vascular system, especially under the simultaneous influence of cytotoxic substances (cytostatic agents, corticoids, diuretics etc.) as the manifestation of a chemoprotective (chemopreventive) effect. This could also be confirmed clinically by an inhibition of the decrease in immunocompetent cells and a demineralization of the hard tissue;
2. the increased tendency of granulo-, erythro-, lympho- and thrombocytopoiesis as well as activation of osteoblasts and osteocytes as an indication of an increased hemato-, angio- and -osteogenesis. This could also be confirmed clinically indirectly by the increase of bone density with a concomitant reduction of the loading pain of the locomotor system;
3. the stimulation of the metabolic performance of hepatocytes as a functional equivalent of a hepatocurative and hepatoprotective action;
4. the decrease of the serum levels of bilirubin, creatinin and urea as an indication of an improvement of renal function and thus of detoxification of the ammonia generated in protein metabolism and, in connection with this reaction cycle, an increased mitochondrial performance of hepatocytes;
5. the decrease of cholesterol and triglyceride values in terms of a positive influence on pathological lipid metabolism disorders and thus reduction of atherogenic risk factors;
6. the reduction of alkaline and acid phosphatase in animal experiments and clinically in terms of a positive influence on pathological disorders of bones, liver, kidneys, intestine or on leucemia or carcinomas;
7. lack of indications of micromorphological structural interferences or pathologically altered organic function in terms of undesired, in particular cancerogenic or mutagenic, effects, as seen from the results of the evaluated hematological, clinical-chemical and histological examinations.

Putamen ovi may be used as oral adjuvants for malignant tumor treatment, especially the treatment of primary and secondary bone tumors with osteoclastic or osteolytic metastases (bone destruction), tumor-like bone defects with intra-ossal space occupation, for the treatment of bone cysts, either alone or in combination with cytostatic agents, especially cyclophosphamide, or radiation therapy. In particular, putamen ovi according to this invention is useful for increasing the tolerance for chemotherapy, cytostatic and radiologic therapies, especially in combination with chemically defined substances selected from cytostatic agents, such as cisplatin, cyclophosphamide, methotrexate, fluorouracil, bleomycin, and/or diuretics, such as acetazolamide, hydrochlorothiazide, chlorothalidone, furosemide, amiloride, for inhibiting the bone substance destruction due to diuresis and saluresis, or as an adjuvant of analgesia, especially as a pharmacological component of the positive influencing of interactions between the endocrine, nervous and immune systems.

As contemplated by this invention, a medicament comprising putamen ovi according to this invention may be used for the inhibition of bone decalcification upon daily cigarette consumption, for the additive treatment of hyperlipoproteinemias, especially hypercholesterolemia and/or hypertriglyceridemia, and/or for the treatment of anemia, especially in tumor patients. Putamen ovi preparations according to this invention may be employed together with mistletoe (Viscum) extracts, Echinacea extracts, especially dry extracts (*E. pallida* and *E. angustifolia*), artichoke (Cynara) extracts and/or nettle (Urtica) extracts, especially dry extracts from the roots, leaves or herbs, further with birch leave (13etula) extracts and with horsetail (Equisetum) extracts and with dandelion (Taraxacum) extracts, also in combination with chemically defined diuretics/cytostatic agents, for the inhibition of bone demineralization and/or depression.

Therapeutic compounds according to this invention are preferably formulated in pharmaceutical compositions containing the compound and a pharmaceutically acceptable carrier. The pharmaceutical composition may contain other components so long as the other components do not reduce the effectiveness of the compound according to this invention so much that the therapy is negated. Pharmaceutically acceptable carriers are well known, and one skilled in the pharmaceutical art can easily select carriers suitable for particular routes of administration (*Remington's Pharmaceutical Sciences*, Mack Publishing Co., Easton, Pa., 1985). The pharmaceutical compositions containing any of the compounds of this invention may be administered by implantation or, preferably, orally.

Dose and duration of therapy will depend on a variety of factors, including disease type, patient age, patient weight, etc. Preferably, initial dose levels will be selected based on their ability to achieve ambient concentrations shown to be effective in in-vitro models, in-vivo models and in clinical trials, up to maximum tolerated levels. The dose of a particular drug and duration of therapy for a particular patient can be determined by the skilled clinician using standard pharmacological approaches in view of the above factors. The response to treatment may be monitored by analysis of blood or body fluid levels or levels in relevant tissues or monitoring disease state in the patient. The skilled clinician will adjust the dose and duration of therapy based on the response to treatment revealed by these measurements.

From the experimental and clinical results described herein, it can be concluded that the recorded changes of defined hematological and clinical-chemical analytical values as well as of morphofunctional clinical pictures of bones and bone marrows, of primary and secondary lymphatic organs, and of liver, pancreas and kidneys, have to be considered under two aspects: the present results speak, on one hand, for the presence of osteopathy-inhibiting effects of the test substance PO, and on the other hand, for novel (as yet unpublished) biological effects which may be used under therapeutic aspects in deficiencies of the cellular immune condition and in disorders of bone metabolism (osteoneogenesis) and of hepatic and renal functions.

EXAMPLES

In order to facilitate a more complete understanding of the invention, a number of Examples are provided below. However, the scope of the invention is not limited to specific embodiments disclosed in these Examples, which are for purposes of illustration only.

Example 1

Preparation of Putamen Ovi

Fifty kilograms of egg-shells from *G. domesticus* were washed 5 times with 250 1 of aqua purificata at 60° C., the suspended matter being, drawn off after each washing. The cleaned egg-shells were dried in a hot-air sterilizer at 165° C. for 4 hours for germ count reduction and sterilization.

The dried egg-shells were ground with a pin-disk mill and separated with a screen having a mesh size of 0.1 mm×0.09 mm.

Putamen ovi was obtained thereby having the following grain size distribution:

| | |
|---|---|
| >0.05 mm | 35% by weight; and |
| <0.01 mm | 65% by weight. |

Using suitable tableting vehicles and citric acid, coated tablets were prepared which contained 440 mg of micronized putamen ovi, corresponding to 160 mg of calcium ions. The amount of citric acid was 1.07 mg.

Example 2

Effects of Putamen Ovi in a Rat Model

Animals and Animal Keeping

Male Wistar rats having an average body weight of 322.5 g were kept under conventional conditions at a room temperature of 21±1° C., a relative atmospheric humidity of about 60% and a 12 hour day/night cycle. Prior to the start of the experiment, they where subjected to an acclimatization to those keeping conditions for 12 days.

Feeding was performed with the pelletized standard diet Altromin C 1000, Misch. Nr. 100 (Altrogge). The animals were given tap water ad libidum as drinking water.

Testing Substances and Dosage

1. Coated tablet core granules, micronized with putamen ovi; 1 coated tablet core aar® os with 640 mg contains 440 mg of putamen ovi, micronized, corresponding to 160 mg of calcium; Dosage form: Putamen ovi, coated tablet core granules, 146 mg (≡100 mg of putamen ovi, micronized≈36.5 mg of Ca) is suspended in 2 ml of dist. water (POS), 0.5 ml (POS)≡9.125 mg of Ca (PO)/250 mg of body weight
2. Calcium carbonate (CC) 91.18 mg of CC≈36.5 mg of Ca 0.5 ml of CCS≈9.125 mg of Ca (CC)/250 mg of body weight
3. Sodium fluoride (NF)
4. Cyclophosphamide (CyS) Dosage form: 1 mg of cyclophosphamide/0.05 ml of dist. water
5. Furosemide (FUR)
6. Cyclophosphamide (CyS)+putamen ovi (PO)
7. Cyclophosphamide (CyS)+calcium carbonate (CC)
8. Cyclophosphamide (CyS)+sodium fluoride (NF)
9. Furosemide (FUR)+putamen ovi (PO)
10. Furosemide (FUR)+calcium carbonate (CC)
11. Furosemide (FUR)+sodium fluoride (NF)

Treatment Groups and Application

Thirty-one male Wistar rats were grouped into the following treatment groups for the examination:

| group | | dose (mg/kg body weight) | number of animals |
|---|---|---|---|
| I | control (comparison) | — | 5 |
| II | PO (invention) | 36.5 | 5 |
| III | CC | 36.5 | 2 |
| IV | NF | 20 | 2 |
| V | CyS | 5 | 2 |
| VI | FUR | 50 | 2 |
| VII | CyS + PO (invention) | 5 + 36.5 | 3 |
| VIII | CyS + CC | 5 + 36.5 | 2 |
| IX | CyS + NF | 5 + 20 | 2 |
| X | FUR + PO (invention) | 50 + 36.5 | 2 |
| XI | FUR + CC | 50 + 36.5 | 2 |
| XII | FUR + NF | 50 + 20 | 2 |

The test substances, PO, CC, NF, CyS, FUR, CyS +PO, CyS+CC, CyS+NF, and FUR+PO, FUR+CC and FUR+NF, were administered to the untranquilized animals intragastrally by means of a rigid button probe once daily for 7 days. The suspension were freshly prepared immediately before the administration and homogeneously administered. The control animals were given physiological saline in an equivalent volume.

Measurement of Hematological and Clinical-chemical Parameters

Peripheral blood was analyzed for 1. cell content:
   erythrocytes (RBC), leucocytes (WBC), platelets (PLT), hemoglobin (HGB), hematocrit (HCT)
2. erythrocyte indices:
   mean cell volume (MCV), mean corpuscular hemoglobin (MCH), mean hemoglobin concentration of erythrocytes (MCHC), and erythrocyte distribution width (RDW)
3. leucocyte differentiation:
   by flow cytometry: granulocytes, monocytes, lymphocytes, B and T cells, helper and suppressor cells
4. serum chemistry:
   GPT, GOT,
   glucose,
   Cholesterol, triglycerides,
   Na, K, Cl, Ca,
   creatinin, urea, total protein.

By means of the fully automated hematology analyzer Sysmex K-1000, the following were determined: WBC, RBC, PLT as well as HGB and HCT, further MCV, MCH and MCHC. The main unit of this device essentially consists of a hydraulic (HS) and an electronic (ES) system. The HS is used for sucking, pipetting, diluting, mixing and lysing. The ES analyzes and converts the signals from the HS and submits the results to the printer. With the aid of microprocessors, the ES also monitors the test runs, the testing station, and performs a quality control.

The hematocrit value corresponds to the percent volume fraction of erythrocytes in blood. In addition to the number of erythrocytes and the hematocrit value, the level of hemoglobin, the chromoprotein contained in the erythrocytes, is an important criterion for the diagnostics of anemias. Classification is performed by the erythrocyte indices. Erythrocyte size and hemoglobin content are characterized by the erythrocyte volume (MCV=mean corpuscular volume), the hemoglobin content of the erythrocytes (MCH=mean corpuscular hemoglobin), and the mean corpuscular hemoglobin concentration (MCHC). The erythrocyte distribution width (RDW=red cell distribution width) is a measure of anisocytosis.

Parameters such as enzymes, glucose, lipids, electrolytes, creatinin, urea and protein are detected selectively, method-oriented, photometrically or ion-selectively using the analyzer Cobas Mira. The supplemental report furnishes analysis-specific data of quality control and statistics.

The leucocyte differentiation was performed using the flow cytometer FACScan following appropriate lysing of the whole blood sample (scattered light measurement).

The lymphocyte differentiation was performed after specific monoclonal incubation by means of fluorescence-activated cell sorting (fluorescence measurement).

On the 7th day of treatment, there were analyzed quantitatively:

leucocytes (total), lymphocytes (total),
T lymphocytes (CD2+/CD45 RA−),
B lymphocytes (CD2−/CD45 RA+),
helper lymphocytes (CD4−/CD8b+),
NK cells (CD8a+/CD8b−).

For determining the phenotypes of the lymphocytes, they were incubated with the following antibodies of Pharmingen, San Diego (USA), to which a fluorochrome was coupled:

Fluorescein isothiocyanate (FITC) conjugated mouse anti-rat CD2 monoclonal antibody,
    R-phycoerythrin (R-PE) conj. mouse anti-rat CD45RA OR A/B monoclonal antibody,
    fluorescein isothiocyanate (FITC) conj. mouse anti-rat CD4 monoclonal antibody,
    R-phycoerythrin (R-PE) conj. mouse anti-rat CD8 ($\beta\beta$ chain) monoclonal antibody,
    fluorescein isothiocyanate (FITC) conj. mouse anti-rat CD8a monoclonal antibody.

| Sample: | a) CD2/CD45RA | = T and B cells |
|---|---|---|
| | b) CD4/CD8b | = $T_4$ and $T_8$ cells |
| | c) CD8a/CD8b | = NK cells |

5 µl each of the antibodies is incubated with 50 µl of Na-EDTA-blood at room temperature in the dark for 20 min. The suspension is agitated with 2 ml of Lyses Reagenz of Becton-Dickinson and incubated for 10 min as described. This followed by centrifuging at 400×g for 6 min, and the supernatant is poured off. The pellet is washed with 3 ml of Cell Wash and centrifuged at 400×g for 6 min. The pellet is taken up in 100 µl of Cell Wash. The suspension is analyzed by means of the flow cytometer.

Clinical observations

During the acclimatization prior to the start of the experiment and in the course of the entire experimental period, the general condition of the animals was examined. In addition, their body weights were determined daily.

Histological examinations

The histological examinations were performed after formaldehyde fixation of the organ samples with paraffin slices (Medim-Plast®) and hematoxylin-eosin staining (H.E.). The following selected organs were subjected to a light-microscopic examination: Peyer's plaques, bone marrow (sternal), thymus, spleen, lymph nodes (mesenterial catchment area) from the defense system, and the parenchyms liver, pancreas and kidneys.

Results

Erythrocytes and leucocytes

The potentials of the test substances, PO, CC, NF, CyS, FUR, CyS+PO, CyS+CC, CyS+NF, and FUR+PO, FUR+CC and FUR+NF, were determined indirectly via their stimulating effect on the number of leucocytes (WBC) and erythrocytes (RBC).

Measurements were performed with the following test substances (corresponding values for the control=100%):

| | WBC | RBC |
|---|---|---|
| PO | changes only within the physiologically normal range | changes only within the physiologically normal range |
| CC | changes only within the physiologically normal range | changes only within the physiologically normal range |
| NF | +13.8% | −5.8% |
| CyS | −51.3% | +12.0% |
| FUR | +61.0% | unchanged |
| CyS + PO | −37.4% | unchanged |
| CyS + CC | −51.8% | unchanged |
| CyS + NF | −39% | +3.6% |
| FUR + PO | n.d. | n.d. |
| FUR + CC | +48.7% | unchanged |
| FUR + NF | unchanged | −5.0% | n.d. = not determined

Bilirubin, Creatinin, Urea, Glucose, Lipids, Electrolytes and Protein

The following clinical-chemical metabolic measurement values were analyzed in a combined method-specific manner: Bilirubin, creatinin, urea, glutamate oxalacetate transaminase (GOT), glutamate pyruvate transaminase (GPT), gamma-glutamyl transferase (GGT), glucose, cholesterol, triglycerides, calcium, sodium, potassium, chloride and total protein.

Measurements were performed with the following test substances (corresponding values for the control=100%):

| | bilirubin | creatinin | urea | glucose | cholesterol | triglycerides |
|---|---|---|---|---|---|---|
| PO | −27.6% | −21.9% | −5.4% | unch. | −9.3% | −11.1% |
| CC | −17.3% | −19.7% | −13.9% | +6.7% | unch. | −7.8% |
| NF | +13.8% | −20.7% | −13.2% | +15.7% | −8.7% | −4.2% |
| CyS | +58.6% | −28.3% | unch. | +5.2% | −25% | +10.1% |

-continued

| | bilirubin | creatinin | urea | glucose | cholesterol | triglycerides |
|---|---|---|---|---|---|---|
| FUR | +20.7% | −49.7% | −7.3% | unch. | −24.9% | −29.6% |
| CyS + PO | −12.6% | −12.2% | unch. | −10.1% | −25.5% | −3.1% |
| CyS + CC | +27.6% | −38.7% | −5.1% | −4.9% | −7.5% | — |
| CyS + NF | +24.1% | −41.1% | −23.4% | +3.4% | −28.5% | — |
| FUR + PO | n.d. | n.d. | n.d. | n.d. | n.d. | n.d. |
| FUR + CC | +27.6% | −21.3% | −27.7% | unch. | −34.9% | −31.7% |
| FUR + NF | +10.3% | −23.7% | −6.6% | −7.4% | −21.5% | −18.0% | n.d. = not determined
unch. = unchanged

Measurements were performed with the following test substances (corresponding values for the control=100%):

| | GLDH | GOT | GPT | AP | SP | Ca |
|---|---|---|---|---|---|---|
| PO | −11.8% | unch. | unch. | −17.7% | −4.4% | unch. |
| CC | +6.7% | −7.1% | unch. | +5.5% | unch. | unch. |
| NF | −17.3% | −9.8% | −9.7% | unch. | −7.5% | unch. |
| CyS | −21.3% | −24.6% | −30.8% | −14.7% | −9.1% | −23.2% |
| FUR | −31.3% | unch. | −24.4% | −13.4% | −9.1% | −28.9% |
| CyS + PO | −27.6% | −13.0% | −24.4% | −13.0% | −4.7% | −33.6% |
| CyS + CC | −35.8% | −3.2% | −23.9% | −24.8% | −6.5% | −36.0% |
| CyS + NF | −25.2% | unch. | −33.1% | −19.6% | −21.5% | −33.6% |
| FUR + PO | unch. | unch. | unch. | unch. | unch. | unch. |
| FUR + CC | −6.4% | −20.4% | −7.3% | −13.2% | −9.1% | −14.1% |
| FUR + NF | unch. | −39.4% | −23.8% | unch. | −13.1% | −17.5% | n.d. = not determined
unch. = unchanged

Lymphocyte differentiation

Measurements were performed with the following test substances (corresponding values for the control=100%):

| | lymphocytes | T lymphocytes | B lymphocytes | helper lymphocytes | supp. lymphocytes | polymorphs |
|---|---|---|---|---|---|---|
| PO | unch. | unch. | +6.9% | −5.4% | +10.9% | +7.1% |
| CC | unch. | unch. | +7.6% | −4.3% | +12.4% | unch. |
| NF | unch. | unch. | +16.5% | unch. | unch. | +61.8% |
| CyS | −55.0% | −51.9% | −79.9% | −45.9% | −30.9% | −28.1% |
| FUR | +60.5% | +46.2% | n.d. | +41.5% | unch. | +65.7% |
| CyS + PO | −39.3% | −20.7% | −64.0% | −21.8% | −14.9% | −24.9% |
| CyS + CC | −58.8% | −46.5% | −79.8% | −47.9% | −46.6% | unch. |
| CyS + NF | −41.9% | −23.4% | −72.4% | −25.4% | −22.3% | −28.3% |
| FUR + PO | +82.6% | +54.9% | n.d. | +47.0% | +50.9% | +62.0% |
| FUR + CC | +44.6% | +46.7% | +47.0% | +52.3% | +41.9% | +93.4% |
| FUR + NF | unch. | −12.1% | +20.0% | −8.3% | −12.6% | n.d. | n.d. = not determined
unch. = unchanged

Evaluation and Conclusions

In the present in vivo study with rats (treatment period 7 days), defined functions of the bones, bone marrow, circulatory and immune systems, and of the liver, pancreas and kidneys could be influenced with putamen ovi, micronized (PO), in a galenic formulation as coated tablet core granules, and also with simultaneous administration of cyclophosphamide (CyS) and furosemide (FUR).

The influence of PO on clinically healthy rats (group II)
The PO test substance employed:
1. had no influence on the increase of average body weight development and of the weights of the spleen and thymus organs of the test animals;
2. induced, in the peripheral blood, a slight increase of the cell counts of polymorphonuclear granulocytes, B and suppressor cells, and a slight decrease in helper cells;
3. resulted, in the bone marrow, in an increased tendency to formation of cell-rich nests of granulo-, erythro-, lympho- and thrombocytopoiesis with functional nuclear swelling and, in addition, in the presence of activated osteocytes (no resting nuclei) and activated osteoblasts, deposited to the trabeculae of cancellous bones;
4. caused, in the thymus, an increase in lymphoblastic cellular elements in the cortex and medulla; it was striking that, due to the increase of the cell number, a corresponding light-optical zone separation into cortex and medulla could not be seen;
5. resulted, in the spleen, in a slight broadening of the marginal zones, especially in the region of the periarterial sheathes (PALS);
6. induced, in the mesenterial lymph node, a considerable increase in lymphocytic cellular elements in the B and T lymphocyte areas and in the medullary strands, so that the corresponding areas did not appear differentiated light-optically in this case too;
7. clearly stimulated the performance of liver metabolism, in morphologic terms, in the form of a functional nuclear swelling with the picture of uniformly sized nuclei (coordination);
8. caused, in the peripheral blood, a decrease in creatinin, bilirubin, urea, GLDH, AP, SP, Cholesterol and triglyceride contents; the calcium level remained unaffected.

The Influence of a Simultaneous Administration of Cyclophosphamide (CyS) and Putamen Ovi (PO)

The simultaneous administration of CyS and PO (group VII):

1. showed a percental decrease of the average body weight development and of the weights of the spleen and thymus organs of the test animals;
2. induced, in the peripheral blood:
   a) as compared with the control values (group I), a decrease in leucocytes (−37.4%) and their subsets (e.g., T lymphocytes: −20.7%) which had a lesser value than that of group V (CyS: WBC−51.3%, e.g., T lymphocytes: −51%) and group VIII (CyS+CC: WBC−51.8%, e.g., T lymphocytes: −46.5%) and group IX (CyS+NF: WBC−39%, e.g., T lymphocytes: −23.4%);
   b) as compared with CyS (group V), an increase in the cell counts of leucocytes (+28.4%), polymorphonuclear granulocytes (+4.3%) and of lymphocytes (+35%), T (+64.8%), B (+69.2%), helper (+44.4%) and suppressor cells (+23.2%), as the manifestation of a cellular chemoprotective effect;
   c) as compared with CyS+CC (group VIII), an increase in the cell counts which correlates with that determined with group V (CyS). i.e., a chemoprotective effect is not present with pure calcium carbonate;
   d) as compared with CyS+NF (group IX), an increase in the cell counts which is smaller than with CyS+PO (group VII);
3. resulted, in the bone marrow, as compared with CyS (group V), in a clearly increased tendency to formation of cell-rich nests (environments) of granulo-, erythro-, lympho- and thrombocytopoiesis (comparable with the cell picture of the control): no remarkable cell count decrease, no indications of a degeneration of nucleated cells, unchanged erythrocytes in the sinuses, i.e., erythrocytes in thorn-apple form (acanthocytes), as encountered under the influence of CyS even in combination with CC and NF, are not present; also in group VII (CyS+PO)—as compared with group II (PO)—there are encountered activated osteocytes and osteoblasts as well as active cell division;
4. caused, in the thymus, as compared with CyS (group V), CyS+CC (group VIII) and CyS+NF (group IX), a clear increase in lymphoblastic cellular elements in the cortex and medulla;
5. resulted, in the spleen, as compared with CyS (group V), CyS+CC (group VIII) and CyS+NF (group IX), in a broadening of the marginal zones, especially in the region of the periarterial sheathes (PALS);
6. stimulated, in the liver cells, as compared with CyS (group V), the metabolic performance, i.e., partial functional nuclear swelling in hepatocytes;
7. induced, in the mesenterial lymph node, as compared with CyS (group V), CyS+CC (group VI) and CyS+NF (group IX), a considerable increase in lymphocytic cellular elements, in particular in the T lymphocyte areas, and in the medullary strands;
8. caused, in the peripheral blood, as compared with CyS (group V), an increase in potassium (+15.6%) and acid phosphatase (+5.8%), so that the latter parameter reached the content level in the serum of the control group.

The test substance calcium carbonate (CC) neither showed positive effects in clinically healthy rats nor chemoprotective effects after a simultaneous administration of cyclophosphamide. The present experimental results confirm the clinically obtained findings from a two-year study with 361 healthy females in post-menopause in which the effect of calcium carbonate and an organic calcium compound on the osteopenic progression of bone density decrease was examined. In contrast to the organic calcium compound, the treatment with pure calcium carbonate showed only a slightly pronounced inhibitory influence on the bone mass losses.

Sodium fluoride (NF) did not induce an effect with respect to an increase in cell number of T, helper or suppressor cells in the terminal vascular system; in contrast, however, the numbers of B lymphocytes and polymorphonuclear granulocytes was increased (selective induction). A chemoprotective effect was seen with NF after a simultaneous administration of CyS in leucocytes in the peripheral blood, but not in the bone marrow.

In healthy animals, the number of erythrocytes was not increased by CC, slightly increased by PO and clearly increased by CyS, but decreased by NF. After the simultaneous administration of CyS and PO, the number of erythrocytes was normalized as compared with the increased values of CyS, i.e., lowered (substance specific release effect of CyS was inhibited). The decreasing effect on the erythrocyte number of NF and the release effect of CyS were counterbalanced after simultaneous administration; in this case, the value correlated with that of the control group, but not with respect to the bone marrow.

Example 3

Clinical Study on the Induction of Osteoneogenesis and on the Reduction of the Loading Pain of the Locomotor System Using tablets prepared according to Example 1, a patient study was conducted to examine whether it is possible to inhibit the progression of a bone density decrease dose-dependently by a PO treatment and even to reverse the effect, i.e., to induce osteoneogenesis.

Patient Study

The clinical examinations observed the effect of PO on osteoneogenesis in 41 female patients with decreased bone density in post-menopause and the decrease of an existing loading pain (pain reduction) of the vertebral column and joints. The results of the study have been obtained from repeated osteodensitometric determinations.

Clinical Tests

With the coated tablets prepared above, clinical tests were performed in which the reduced bone density was examined with 41 female patients in postmenopause. The coated tablets were administered 3 times a day in the course of 304 days. An increase in bone density in the total universe of 9.4% after 304 days (as an average) was established. The test results are derived from repeated osteodensitometric determinations, the follow-ups of which were additionally supplemented by the detection of the biochemical markers of the bone destruction (osteoclast activity) and activity of bone formation (osteoblast activity).

Osteodensitometry

The bone mineral density measurements were performed using quantitative digital radiography (Hologic QDR-1000 TM bone densitometer) on the lumbar vertebrae (LW 1-4), the result of the bone mineral density calculation being expressed in grams of calcium hydroxyapatite per $cm^2$. In this osteodentitometric method, the measured value is corrected for absorption in the soft-tissue coat; thus, the bone mineral content can be determined without soft-tissue errors.

Initial Examination of the Lumbar Vertebral Column (LW 1-4) in Female Patients in Post-menopause (at Least Six Months from the Last Menstruation)

The results of the initial densitometric examination of a larger universe of patients were compared age-specifically on the basis of reference data (nearly 1000 lumbar vertebral column measurements). The measured bone density (g/cm$^2$) was also given as a percentage of the corresponding age-specific reference value. Subsequently, 41 female patients in post-menopause having a detected bone density of between 61 and 92% were included in the study.

Comparison of Two Vertebral Column Scans for Follow-up

During the phase of therapy with PO, no additional hormone, vitamin $D_3$, calcitonin or other calcium preparations were administered. For the follow-up of the therapeutic effect of PO in the 41 selected patients with decreased bone density in post-menopause, the respective value measured after the end of the therapy was compared with that of therapy start. This absolutely required that the measuring fields of the vertebral column scans in the two analyses be identically adjusted with respect to size, shape and position. A Holgic-specific computer-controlled comparing device was employed in which the measuring field of the repeated examination is set in an optically identical manner with that of the initial examination by matching it to the stored scan. Thus, the reproducibility of the accuracy of measurement is optimized. This method thus ensures that changes in the measured values at different times must be predominantly caused by changes in the bone metabolism.

Results

The overall balance of the osteodensitometric follow-up values on the basis of the 41 follow-up examinations of the effectivity of PO showed an average increase of bone mineral density by +9.4% (from 78.1% to 85.5%). In group A, which was administered PO for less than 200 days, the bone density increased by an average of 5.5%. In group B, which was administered PO for less than 300 days, the measured value increased by 7.3%, and in group C (more than 300 days), the measured value increased by 9.4%. The increases of the measured values obtained after the end of the therapy in patient group A (bone density prior to start of therapy>80%) and group B (<80%) are clearly different. The results show a clear dose-action relationship: in the first group (A), the value increased by 6.9% with administration of 3×1 coated tablet of PO per day, and in the second group (B), it increased by 10.9% with 3×2 coated tablets of PO per day.

The efficiency of PO therapy in decreased bone mineral density in post-menopause (responder/non-responder ratio) is as follows: With 12 of the patients examined, the increase of bone density was less than 5%, with 18 patients, it was between 5 and 10%, and with 11 patients, the value was more than 10% (+15.4%). The responder rate can thus be assumed to be about 70% (B+C). In none of the patients was the bone density after the end of the therapy inferior to that of the initial examination.

Discussion

By a therapy with PO, it is evidently possible to generally counteract a bone density decrease in the vertebral column of female patients in post-menopause. In addition, the study showed that the extent of the increase of bone mineral density is dependent on both the level of daily dose and the duration of the PO therapy.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. It will be understood by those skilled in the art that variations and modifications may readily be made within the scope of this invention as defined by the appended claims.

I claim:

1. A method for the preparation of putamen ovi having a grain size of less than 0.1 mm comprising:
    washing egg shells with purified water while stirring, said washing occurring at at least an ambient temperature;
    autoclaving said egg shells, said autoclaving separating egg shell components of a central palisade zone of said egg shells from an inner and outer shell membrane of said egg shell;
    drying said egg shells; and
    crushing said egg shells to the desired grain size.

2. The method of claim 1, wherein said egg shells are from *Gallus domesticus*.

3. The method of claim 1, wherein said step of crushing said egg shells to a desired grain size comprises:
    grinding said dried egg shells with a pin-disk mill; and
    screening said ground egg shells with a mesh size of 0.1 mm×0.09 mm.

4. The method of claim 1, wherein said step of autoclaving comprises autoclaving at greater than 1 atmosphere for at least 6 hours.

5. Putamen ovi made by the process of claim 1, and having a grain size distribution of:

| | |
|---|---|
| >0.05 mm | 35% by weight, and |
| <0.01 mm | 65% by weight. |

6. A medicament for treatment of a disorder selected from the group consisting of bone marrow development disorders, bone marrow dysfunctions and dyshematopoiesis, osteopenia, dental build-up disorders, spasmophilia, bone fractions, callus formation, calcium deficiency symptoms during growth, calcium deficiency symptoms during pregnancy, calcium deficiency symptoms during postmenopause, and calcium deficiency symptoms during nursing period, said medicament containing an effective amount of putamen ovi made by the process of any one of claims 1–4.

7. A medicament according to claim 6, for oral or local application as a material for bone remodeling and implantation wherein the medicament is used for a bone cement and bone replacement with an osteoneogenesis-active potential for local bone formation; for the reconstruction of bony deficiencies; for the healing of fractures; for the filling of bone damages after tumor operations; for the removal of bone damages in oral surgery and plastic surgery of the face; or for the local induction of osteoneogenesis by the application of extracorporal shock waves in combination with oral administration of putamen ovi for additive enhancement of the osteoneogenetic potential.

8. A method for the treatment of bone marrow development disorders, bone marrow dysfunctions and dyshematopoiesis, osteopenia, dental build-up disorders, spasmophilia, bone fractures, callus formation, calcium deficiency symptoms during growth, calcium deficiency symptoms during pregnancy, calcium deficiency symptoms during postmenopause or calcium deficiency symptoms during nursing period, comprising administration of an effective amount of putamen ovi according to any one of claims 1 to 4 to a patient in need thereof.

9. A method according to claim 8, wherein the patient is suffering from primary or secondary disorders or damages
- of chondral or desmal ossification,
- of the bony substance with external Substantia corticalis and internal Substantia spongiosa as well as bone marrow due to a reduction of all hematopoietic cell forms due to a cytostatic or radiologic therapy or after radiation accidents,
- of the skeleton including osteocytes, intercellular substance with collagenous fibrils and calcified cement, or
- of bone metabolism including the function of osteoclasts and osteoblasts, and the balance between bone absorption and formation.

10. A method according to claim 9, wherein the patient is suffering from primary or secondary disorders or damages of chondral or desmal ossification, and putamen ovi is administered in combination with sodium fluoride and hormones, calcitonin, pyrophosphates, or vitamins.

11. A method for the stimulation of osteoneogenesis or for early callus formation in dentistry, oral and bone surgery, comprising oral or local application of an effective amount of a medicament according to claim 6.

12. A method for the inhibition of bone decalcification upon daily cigarette consumption, comprising administration of an effective amount of a medicament according to claim 6.

13. The method of claim 1, wherein said step of autoclaving is performed discontinuously.

14. The method of claim 1, wherein said step of autoclaving separates said egg shell components of a central palisade zone an inner and outer shell membrane of said egg shell, and from a shell matrix of said central palisade zone of said egg shell.

15. The method of claim 1, wherein said step of crushing said egg shells to the desired grain size comprises crushing said egg shells to a grain size of less than 0.1 mm.

* * * * *